United States Patent
Wu et al.

(10) Patent No.: US 10,890,586 B2
(45) Date of Patent: Jan. 12, 2021

(54) METHODS AND KITS FOR ASSAYING ENDOGLYCOSIDASE ACTIVITY

(71) Applicant: Bio-Techne Corporation, Minneapolis, MN (US)

(72) Inventors: Zhengliang L. Wu, Edina, MN (US); Xinyi Huang, New Brighton, MN (US); Cheryl M. Ethen, Arden Hills, MN (US)

(73) Assignee: BIO-TECHNE CORPORATION, Minneapolis, MN (US)

( * ) Notice: Subject to any disclaimer, the term of this patent is extended or adjusted under 35 U.S.C. 154(b) by 268 days.

(21) Appl. No.: 15/725,835

(22) Filed: Oct. 5, 2017

(65) Prior Publication Data

US 2018/0095084 A1 Apr. 5, 2018

Related U.S. Application Data

(60) Provisional application No. 62/404,359, filed on Oct. 5, 2016.

(51) Int. Cl.
*G01N 33/58* (2006.01)
*C12Q 1/34* (2006.01)
(Continued)

(52) U.S. Cl.
CPC .............. *G01N 33/573* (2013.01); *C12Q 1/34* (2013.01); *C12Q 1/48* (2013.01);
(Continued)

(58) Field of Classification Search
CPC .................................. C12Q 1/48; G01N 33/58
See application file for complete search history.

(56) References Cited

U.S. PATENT DOCUMENTS

| 5,332,812 A | 7/1994 | Nicolson et al. |
| 7,759,314 B2 * | 7/2010 | Fallon ............... A61K 38/1703 514/17.2 |
| 2006/0127945 A1 | 6/2006 | Preaudat et al. |

FOREIGN PATENT DOCUMENTS

WO 2008055575 A1 5/2008

OTHER PUBLICATIONS

Yamaguchi et al. ("Novel proteoglycan glycotechnology: chemoenzymatic synthesis of chondroitin sulfate-containing molecules and its application", Glycoconj. J. (2010) 27:189-198) (Year: 2010).*

(Continued)

*Primary Examiner* — Tracy Vivlemore
*Assistant Examiner* — Nam P Nguyen
(74) *Attorney, Agent, or Firm* — Mueting Raasch Group

(57) ABSTRACT

A method for assaying endoglycosidase activity includes providing a proteoglycan having a glycosaminoglycan chain with a non-reducing end; treating the proteoglycan with a glycosyltransferase to incorporate a carbohydrate into the non-reducing end of the glycosaminoglycan chain, wherein the carbohydrate includes a click chemistry moiety; adding a label to the proteoglycan, wherein the label includes a click chemistry moiety that reacts to the click chemistry moiety of the carbohydrate such that the label attaches to the carbohydrate to form a labeled proteoglycan; immobilizing the labeled proteoglycan on a multi-well plate, wherein the multi-well plate includes a specific anti-proteoglycan antibody for binding the labeled proteoglycan; treating the labeled proteoglycan with an endoglycosidase specific to the glycosaminoglycan chain; and detecting the labeled proteoglycan.

19 Claims, 7 Drawing Sheets

(51) Int. Cl.
G01N 33/573 (2006.01)
C12Q 1/48 (2006.01)
(52) U.S. Cl.
CPC ..... *C12Y 111/01007* (2013.01); *C12Y 204/01* (2013.01); *C12Y 302/01166* (2013.01); *G01N 33/582* (2013.01); *G01N 2333/908* (2013.01); *G01N 2333/91091* (2013.01); *G01N 2333/91097* (2013.01); *G01N 2333/924* (2013.01)

(56) References Cited

OTHER PUBLICATIONS

Ahn SC, Kim BY, Oh WK, Park YM, Kim HM, Ahn JS. 2006. Colorimetric heparinase assay for alternative anti-metastatic activity. Life sciences, 79:1661-1665.
Behzad et al., "A multiwall format assay for heparanase," Analytical Biochemistry, vol. 320, 2003, pp. 2007-213.
Bernfield et al., "Functions of Cell Surface Heparan Sulfate Proteoglycans," Annu. Rev. Biochem., vol. 68, 1999, pp. 729-777.
Breton et al., "Structures and mechanisms of glycosyltransferases," Glycobiology, vol. 16, No. 2, 2006, pp. 29R-37R.
Busse et al., "In Vitro Polymerization of Heparan Sulfate Backbone by the EXT Proteins," The Journal of Biological Chemistry, vol. 278, No. 42, Oct. 2003, pp. 41333-41337.
Dowd et al., "Heparan Sulfate Mediates bFGF Transport through Basement Membrane by Diffusion with Rapid Reversible Binding," The Journal of Biological Chemistry, vol. 274, No. 8, Feb. 1999, pp. 5236-5244.
Esko et al., "Molecular diversity of heparan sulfate," The Journal of Clinical Investigation, vol. 108, No. 2, Jul. 2001, pp. 169-173.
Ethen et al., "GAG-specific Endoglycosidase Assay using 35S-Labeled Proteoglycans," RND Systems, Poster, 2011, 1 page.
Freeman et al., "A rapid quantitative assay for the detection of mammalian heparanase activity," Biochem. J., vol. 325, 1997, pp. 229-237.
Goldshmidt O, Nadav L, Aingorn H, Irit C, Feinstein N, Ilan N, Zamir E, Geiger B, Vlodavsky I, Katz BZ. 2002. Human heparanase is localized within lysosomes in a stable form. Experimental cell research, 281:50-62.
Hammond E, Li CP, Ferro V. 2010. Development of a colorimetric assay for heparanase activity suitable for kinetic analysis and inhibitor screening. Analytical biochemistry, 396:112-116.
Hulett et al., "Cloning of mammalian heparanase, an important enzyme in tumor invasion and metastasis," Nature Medicine, vol. 5, No. 7, Jul. 1999, pp. 803-809.
International Patent Application No. PCT/US2017/054738, International Search Report and Written Opinion dated Dec. 8, 2017, 13 pages.
Kolb HC, Finn MG, Sharpless KB. 2001. Click Chemistry: Diverse Chemical Function from a Few Good Reactions. Angewandte Chemie, 40:2004-2021.
Mao et al., "A Liquid Chromatography-Mass Spectrometry Based Approach to Characterize the Substrate Specificity of Mammalian Heparanase," The Journal of Biological Chemistry, vol. 289, No. 49, 2014, 30 pages.
Nadir Y, Vlodavsky I, Brenner B. 2008. Heparanase, tissue factor, and cancer. Seminars in thrombosis and hemostasis, 34:187-194.
Nakajima M, Irimura T, Di Ferrante D, Di Ferrante N, Nicolson GL. 1983. Heparan sulfate degradation: relation to tumor invasive and metastatic properties of mouse B16 melanoma sublines. Science, 220:611-613.
Nakajima et al., "Metastatic Melanoma Cell Heparanase: Characterization of heparan sulfate degradation fragments produced by B16 melanoma endoglucuronidase," The Journal of Biological Chemistry, vol. 259, No. 4, Feb. 1984, pp. 2283-2290.
Nakajima et al., "Suramin: A potent inhibitor of melanoma heparanase and invasion," The Journal of Biological Chemistry, vol. 266, May 1991, pp. 9661-9666.
Nakajima M, Irimura T, Nicolson GL. 1988. Heparanases and tumor metastasis. Journal of cellular biochemistry, 36:157-167.
Pala et al., "Kinetic analysis and molecular modeling of the inhibition mechanism of roneparstat (SST0001) on human heparanase," Glycobiology, vol. 26, No. 6, 2016, pp. 640-654.
Ramani et al., "The heparanase/syndecan-1 axis in cancer: mechanisms and therapies," Author Manuscript, FEBS J., vol. 280, No. 10, May 2013, pp. 2294-2306.
Schoenfeld AK, Vierfuss S, Luhn S, Alban S. 2014. Testing of potential glycan-based heparanase inhibitors in a fluorescence activity assay using either bacterial heparinase II or human heparanase. Journal of pharmaceutical and biomedical analysis, 95:130-138.
Shi et al., "LC-MS and LC-MS/MS studies of incorporation of 34SO3 into glycosaminoglycan chains by sulfotransferases," Glycobiology, 2013, pp. 1-11.
Shi X, Zaia J. 2009. Organ-specific heparan sulfate structural phenotypes. The Journal of biological chemistry, 284:11806-11814.
Staples GO, Shi X, Zaia J. 2010. Extended N-sulfated domains reside at the nonreducing end of heparan sulfate chains. The Journal of biological chemistry, 285:18336-18343.
Tsuchida S, Podyma-Inoue KA, Yanagishita M. 2004. Ultrafiltration-based assay for heparanase activity. Analytical biochemistry, 331:147-152.
Vlodavsky I, Elkin M, Abboud-Jarrous G, Levi-Adam F, Fuks L, Shafat I, Ilan N. 2008. Heparanase: one molecule with multiple functions in cancer progression. Connective tissue research, 49:207-210.
Vlodavsky I, Friedmann Y. 2001. Molecular properties and involvement of heparanase in cancer metastasis and angiogenesis. The Journal of clinical investigation, 108:341-347.
Vlodavsky I, Friedmann Y, Elkin M, Aingorn H, Atzmon R, Ishai-Michaeli R, Bitan M, Pappo O, Peretz T, Michal I, et al. 1999. Mammalian heparanase: gene cloning, expression and function in tumor progression and metastasis. Nat Med, 5:793-802.
Vlodavsky I, Goldshmidt O, Zcharia E, Atzmon R, Rangini-Guatta Z, Elkin M, Peretz T, Friedmann Y. 2002. Mammalian heparanase: involvement in cancer metastasis, angiogenesis and normal development. Seminars in cancer biology, 12:121-129.
Woods A, Couchman JR. 1994. Syndecan 4 heparan sulfate proteoglycan is a selectively enriched and widespread focal adhesion component. Molecular biology of the cell, 5:183-192.
Wu ZL, Huang X, Burton AJ, Swift KA. Probing sialoglycans on fetal bovine fetuin with azido-sugars using glycosyltransferases. Glycobiology, vol. 26, No. 4, 2016, pp. 329-334.
Wu ZL, Lech M. 2005. Characterizing the non-reducing end structure of heparan sulfate. The Journal of biological chemistry, 280:33749-33755.
Xu D, Esko JD. 2014. Demystifying heparan sulfate-protein interactions. Annual review of biochemistry, 83:129-157.
Zetser A, Levy-Adam F, Kaplan V, Gingis-Velitski S, Bashenko Y, Schubert S, Flugelman MY, Vlodavsky I, Ilan N. 2004. Processing and activation of latent heparanase occurs in lysosomes. Journal of cell science, 117:2249-2258.
Zhang JH, Chung TD, Oldenburg KR. 1999. A Simple Statistical Parameter for Use in Evaluation and Validation of High Throughput Screening Assays. Journal of biomolecular screening, 4:67-73.
Wray W, Boulikas T, Wray VP, Hancock R. 1981. Silver staining of proteins in polyacrylamide gels. Analytical biochemistry, 118:197-203.
Wu ZL, Huang X, Burton AJ, Swift KA. 2015a. Glycoprotein labeling with click chemistry (GLCC) and carbohydrate detection. Carbohydrate research, 412:1-6.

* cited by examiner

METHODS AND KITS FOR ASSAYING ENDOGLYCOSIDASE ACTIVITY

CROSS-REFERENCE

This application claims priority to U.S. Provisional Application No. 62/404,359, filed Oct. 5, 2016, the entire contents of which are incorporated herein by reference.

TECHNICAL FIELD

This disclosure relates to methods for assaying endoglycosidase activity, and more particularly, to methods for assaying heparanase activity.

BACKGROUND

Glycosaminoglycans (GAGs) are linear amino-polysaccharides found in the extracellular matrix and on the cell membrane. They include heparan sulfate (HS), heparin, chondroitin sulfate (CS), dermatan sulfate (DS), keratan sulfate (KS) and hyaluronan (HA). The majority of GAGs exist as components of functional proteoglycans. Proteoglycans consist of a protein core with attached GAG chains. GAGs play roles in numerous cellular events, including cell growth, migration, and signaling through interaction with various growth factors, cytokines and other extracellular matrix proteins. Regulation of GAG synthesis and degradation is essential for these related cellular events. In mammals, GAG degradation is accomplished by GAG-specific endoglycosidases. For example, HS is degraded by Heparanase (HPSE), HA is degraded by Sperm Adhesion Molecule 1 (SPAM1) and Hyaluronidase 1 (HYAL1), and CS is degraded by Hyaluronidase 4 (HYAL4). These enzymes are key to furthering the understanding of GAG degradation and subsequent cellular events.

A number of assays have been developed for studying endoglycosidase activity, including radioisotope assays, colorimetric assays, fluorescent assays, and enzyme-linked immunosorbent assay (ELISA)-based assays. These assays rely on internal labeling of GAGs, which can interfere with the digestion of the GAGs by GAG-specific endoglycosidases and make it difficult to accurately assay GAG-specific endoglycosidase activity. As a result, there are no quantitative assays for measuring GAG-specific endoglycosidase activity and few known drugs or therapeutic agents for inhibiting GAG-specific endoglycosidase activity.

SUMMARY

In general, this disclosure relates to methods and kits for assaying endoglycosidase activity. Non-reducing ends of glycosamininoglycan (GAG) chains on a proteoglycan are labeled using a GAG polymerase. The labeled sample is subsequently biotinylated using click chemistry and immobilized on a multi-well plate. A GAG-specific endoglycosidase is added to the biotinylated sample, and the endoglycosidase removes the label from the GAG chains. The biotinylated sample is detected using enzyme-linked immunosorbent assay (ELISA). The removal of the label from the GAG chains by the GAG-specific endoglycosidase results in a reduced signal detected by ELISA. By labeling the non-reducing ends of the GAG chains, any interference with the digestion of the GAG chains by the GAG-specific endoglycosidase due to internal labeling is eliminated. This assay is highly sensitive and reproducible, and thus suitable for screening potential GAG-specific endoglycosidase inhibitors and activators.

In one embodiment, a method for assaying endoglycosidase activity includes providing a proteoglycan having a glycosaminoglycan chain with a non-reducing end; treating the proteoglycan with a glycosyltransferase to incorporate a carbohydrate into the non-reducing end of the glycosaminoglycan chain, wherein the carbohydrate includes a click chemistry moiety; adding a label to the proteoglycan, wherein the label includes a click chemistry moiety that reacts to the click chemistry moiety of the carbohydrate such that the label attaches to the carbohydrate to form a labeled proteoglycan; immobilizing the labeled proteoglycan on a multi-well plate, wherein the multi-well plate includes a specific anti-proteoglycan antibody for binding the labeled proteoglycan; treating the labeled proteoglycan with an endoglycosidase specific to the glycosaminoglycan chain; and detecting the labeled proteoglycan.

In another embodiment, a method for assaying heparanase activity includes providing a human Syndecan-4 having a heparan sulfate with a non-reducing end; treating the Syndecan-4 with EXT1/2 to incorporate GlcNAz into the non-reducing end of the heparan sulfate chain, wherein the GlcNAz includes an azido group click chemistry moeity; adding a label to the Syndecan-4, wherein the label includes an alkyne group click chemistry moiety that reacts to the click chemistry moiety of the GlcNAz such that the label attaches to the GLcNAz to form a labeled Syndecan-4; immobilizing the labeled Syndecan-4 on a multi-well plate, wherein the multi-well plate includes a specific anti-Syndecan-4 antibody for binding the labeled Syndecan-4; treating the labeled Syndecan-4 with heparanase; and detecting the labeled Syndecan-4.

In another embodiment, a kit for assaying endoglycosidase activity includes a proteoglycan having a glycosaminoglycan chain with a non-reducing end, a glycosyltransferase, a carbohydrate with a click chemistry moiety, a label including a click chemistry moiety that reacts to the click chemistry moiety of the carbohydrate such that the label attaches to the carbohydrate, an endoglycosidase specific to the glycosaminoglycan chain, a specific anti-proteoglycan antibody for binding the labeled proteoglycan, a multi-well plate, click chemistry reagents, and a reporter molecule.

In another embodiment, a method of screening a test substance as an inhibitor of endoglycosidase activity includes immobilizing a labeled proteoglycan on a multi-well plate, wherein the multi-well plate includes a specific anti-proteoglycan antibody for binding the labeled proteoglycan and wherein carbohydrates having a click chemistry moiety are incorporated into non-reducing ends of glycosaminoglycan chains on the proteoglycan and labels including a click chemistry moiety that reacts to the click chemistry moiety of the carbohydrates are attached to the carbohydrates; combining the test substance and an endoglycosidase specific to the glycosaminoglycan chain in a buffer solution to form a test substance/endoglycosidase mixture; adding the test substance/endoglycosidase mixture to the immobilized labeled proteoglycan in the multi-well plate; incubating the multi-well plate; measuring the absorbance of the labeled proteoglycan in the presence of the test substance/endoglycosidase mixture; comparing the absorbance of the labeled proteoglycan in the presence of the test substance/endoglycosidase mixture with the absorbance of the labeled proteoglycan in the presence of the endoglycosidase without the test substance; and designating the test substance as an inhibitor of the endoglycosidase when the absorbance of the labeled proteoglycan in the presence of the test substance/endoglycosidase mixture is greater than the absorbance of the labeled proteoglycan in the presence of the endoglycosidase without the test substance.

In another embodiment, a method of screening a test substance as a therapeutic agent for treating cancer includes immobilizing a labeled recombinant Syndecan-4 on a multi-well plate, wherein the multi-well plate includes a specific anti-Syndecan-4 antibody for binding the labeled Syndecan-4 and wherein GlcNAz having an azido group click chemistry moeity is incorporated into non-reducing ends of heparan sulfate on the Syndecan-4 and labels including an alkyne group click chemistry moiety that reacts to the click chemistry moiety of the GlcNAz are attached to the carbohydrates; combining a test substance and heparanase in a buffer solution to form attest substance/heparanase mixture; adding the test substance/heparanase mixture to the immobilized labeled recombinant Syndecan-4 in the multi-well plate; incubating the multi-well plate; measuring the absorbance of the labeled Syndecan-4 in the presence of the test sub stance/heparanase mixture; comparing the absorbance of the labeled Syndecan-4 in the presence of the test substance/heparanase mixture with the absorbance of labeled Syndecan-4 in the presence of the heparanase without the test substance; and designating the test substance as a therapeutic agent for treating cancer when the absorbance of the labeled Syndecan-4 in the presence of the test substance/heparanase mixture is greater than the absorbance of labeled Syndecan-4 in the presence of the heparanase without the test substance.

In another embodiment, a method of determining whether a test substance affects the activity of an endoglycosidase includes immobilizing a labeled proteoglycan on a multi-well plate, wherein the multi-well plate includes a specific anti-proteoglycan antibody for binding the labeled proteoglycan and wherein carbohydrates having a click chemistry moiety are incorporated into non-reducing ends of glycosaminoglycan chains on the proteoglycan and labels including a click chemistry moiety that reacts to the click chemistry moiety of the carbohydrates are attached to the carbohydrates; combining a test substance and an endoglycosidase specific to the glycosaminoglycan chain in a buffer solution to form a test substance/endoglycosidase mixture; adding the test substance/endoglycosidase mixture to the immobilized labeled recombinant proteoglycan in the multi-well plate; incubating the multi-well plate; measuring the absorbance of the labeled proteoglycan in the presence of the test substance/endoglycosidase mixture; and comparing the absorbance of the labeled proteoglycan in the presence of the test substance/endoglycosidase mixture with the absorbance of the labeled proteoglycan in the presence of the endoglycosidase without the test substance.

In another embodiment, a method of determining a half-maximal effective value of a test substance for inhibiting the activity of an endoglycosidase includes immobilizing a labeled proteoglycan on a multi-well plate, wherein the multi-well plate includes a specific anti-proteoglycan antibody for binding the labeled proteoglycan and wherein carbohydrates having a click chemistry moiety are incorporated into non-reducing ends of glycosaminoglycan chains on the proteoglycan and labels including a click chemistry moiety that reacts to the click chemistry moiety of the carbohydrates are attached to the carbohydrates; combining a test substance and an endoglycosidase specific to the glycosaminoglycan chain in a buffer solution to form a test substance/endoglycosidase mixture; adding the test substance/endoglycosidase mixture to the immobilized labeled recombinant proteoglycan in the multi-well plate; incubating the multi-well plate; measuring the absorbance of the labeled proteoglycan in the presence of the test substance/ endoglycosidase mixture; and using the measured absorbance to calculate the half-maximal effective value of the test substance for inhibiting the activity of the endoglycosidase.

In another embodiment, a method of determining a half-maximal effective value of a test substance for activating the activity of an endoglycosidase includes immobilizing a labeled proteoglycan on a multi-well plate, wherein the multi-well plate includes a specific anti-proteoglycan antibody for binding the labeled proteoglycan and wherein carbohydrates having a click chemistry moiety are incorporated into non-reducing ends of glycosaminoglycan chains on the proteoglycan and labels including a click chemistry moiety that reacts to the click chemistry moiety of the carbohydrates are attached to the carbohydrates; combining a test substance and an endoglycosidase specific to the glycosaminoglycan chain in a buffer solution to form a test substance/endoglycosidase mixture; adding the test substance/endoglycosidase mixture to the immobilized labeled recombinant proteoglycan in the multi-well plate; incubating the multi-well plate; measuring the absorbance of the labeled proteoglycan in the presence of the test substance/ endoglycosidase mixture; and using the measured absorbance to calculate the half-maximal effective value of the test substance for activating the activity of the endoglycosidase.

The details of one or more examples are set forth in the accompanying drawings and the description below. Other features, objects, and advantages will be apparent from the description and drawings, and from the claims.

DETAILED DESCRIPTION

The following detailed description is exemplary in nature and is not intended to limit the scope, applicability, or configuration of the disclosure in any way. Rather, the following description provides some practical illustrations for implementing examples of the present disclosure. Examples of constructions, materials, dimensions, and manufacturing processes are provided for selected elements, and all other elements employ that which is known to those of ordinary skill in the field of the disclosure. Those skilled in the art will recognize that many of the noted examples have a variety of suitable alternatives.

Figure 1:
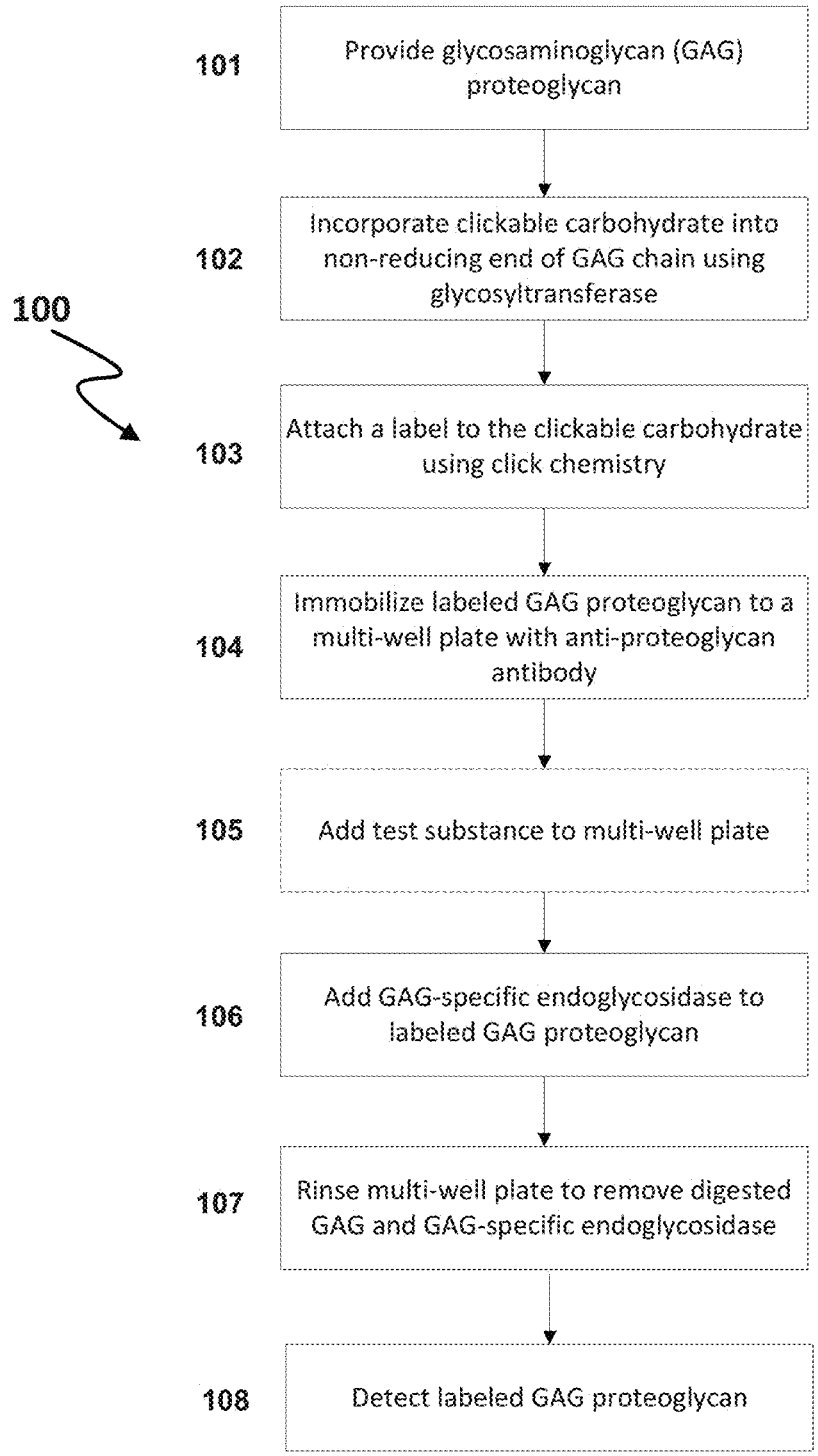
FIG. 1 is a flow diagram of a method for assaying endoglycosidase activity according to various embodiments.

FIG. 1 is a flow diagram of method 100 for assaying endoglycosidase activity. Method 100 can include providing a glycosaminoglycan (GAG) proteoglycan (101), incorporating a clickable carbohydrate into the non-reducing end of the GAG chains of the proteoglycan using a glycosyltransferase (102), attaching a label to the clickable carbohydrate using click chemistry (103), immobilizing the labeled proteoglycan to a multi-well plate with an anti-proteoglycan antibody (104), adding a test substance to the multi-well plate (105), adding a GAG-specific endoglycosidase to the labeled GAG proteoglycan (106), rinsing the multi-well plate to remove digested GAG and the GAG-specific endoglycosidase (107), and detecting the labeled GAG proteoglycan (108).

The steps of method 100 are not limited to the order shown in FIG. 1. For example, in some embodiments, the GAG-specific endoglycosidase can be added to the labeled GAG proteoglycan (106) prior to immobilizing the labeled GAG proteoglycan to a multi-well plate (104). Additionally, method 100 need not include all of the steps shown in FIG. 1. For example, in some embodiments, method 100 may exclude the step of adding a test substance to a multi-well plate (105).

Method 100 allows for assaying endoglycosidase activity by labeling the non-reducing ends of GAG chains on a proteoglycan. When an endoglycosidase is added to a labeled proteoglycan, the endoglycosidase digests the GAG chains, thus removing the label from the GAG chains. The removal of the label from the GAG chains by the endoglycosidase results in a reduced detection signal. As a result, endoglycosidase activity can be quantified based on the detection signal of the labeled proteoglycan. Method 100 is advantageous, because it can be used to label all types of GAG chains and thus assay the activity of their corresponding endoglycosidases. Method 100 can thus be used to screen potential therapeutic agents, such as inhibitors and/or activators of endoglycosidases, for applications in treatment of cancer, reducing inflammation, and healing wounds.

In some embodiments of method 100, the GAG proteoglycan can be a recombinant GAG proteoglycan. In some embodiments, the GAG proteoglycan can be one of Syndecan-1, Syndecan-2, Syndecan-3, Syndecan-4, Glypican-1, Glypican-2, Glypican-3, Glypican-4, Glypican-5, Glypican-6, lumican, mimican, aggrecan, Testican 1, Testican 2, and Testican 3. The GAG chains on the proteoglycan can include heparan sulfate (HS), heparin, chondroitin sulfate (CS), dermatan sulfate (DS), keratan sulfate (KS), or hyaluronan (HA). It has been discovered that these GAG chains all have non-reducing ends into which a clickable carbohydrate can be incorporated, thus allowing for end labeling of the GAG chains for detection. By labeling the non-reducing ends of the GAG chains, any interference with the digestion of the GAG chains by the GAG-specific endoglycosidase due to internal labeling is eliminated.

A glycosyltransferase is used to incorporate a clickable carbohydrate into the non-reducing end of a GAG chain on the recombinant proteoglycan (102). In some embodiments, the glycosyltransferase can be a recombinant glycosyltransferase. In some embodiments, the glycosyltransferase can be GlcNAc transferase, GalNAc transferase, galactosyltransferase, glucuronosyltransferase, or combinations thereof. The clickable carbohydrate includes a click chemistry moiety that can be used in a click chemistry reaction, such as an azido or an alkyne group. In some cases, the carbohydrate is a monosaccharide. It has been discovered that azidoacetylglucosamine (GlcNAz), which includes an azido group, is a suitable clickable carbohydrate for incorporation into the non-reducing end of heparin sulfate, hyaluronan, and karatan sulfate. Additionally, azidoacetylgalactosamine (GalNAz) is a suitable clickable carbohydrate for incorporation into the non-reducing end of chondroitin sulfate.

Once the clickable carbohydrate is incorporated into the GAG chains on the proteoglycan, a label is attached to the clickable carbohydrate through a click chemistry reaction (103) to form a labeled proteoglycan. Click chemistry is a way to quickly and reliably join small units together. It is not a single specific reaction, but refers to a general way of joining small modular units. The label includes a click chemistry moiety that reacts to the click chemistry moiety of the incorporated carbohydrate such that the label attaches to the carbohydrate. In some embodiments, the carbohydrate includes an azido group and the label includes an alkyne group. In other embodiments, the carbohydrate includes an alkyne group and the label includes an azido group. The clickable label can be a reporter molecule, such as a colorimetric label, a biotin label, a luminescent label or a fluorescent label.

Upon attachment of the label to the GAG chains of the proteoglycan, the labeled proteoglycan can be used to assay the activity of various endoglycosidases corresponding to the GAG chains on the proteoglycan. In some embodiments, the endoglycosidase can be a recombinant endoglycosidase. In some embodiments, the endoglycosidase can be heparanase (HPSE), sperm adhesion molecule 1, hyaluronidase 1, hyaluronidase 2, hyaluronidase 3, hyaluronidase 4, or keratan sulfate specific endo-beta-galactosidase. In order to assay the activity of an endoglycosidase, the labeled proteoglycan must be immobilized (104). In some embodiments, the labeled proteoglycan is immobilized to a multi-well plate or a microtiter plate, such as a 96-well plate, for use in systems such as an enzyme-linked immunosorbent assay (ELISA). The multi-well plate can, for example, be coated with an anti-proteoglycan antibody which captures the corresponding proteoglycan and immobilizes the proteoglycan on the plate. This indirectly immobilizes the GAG chains to the multi-well plate through the core protein of the labeled proteoglycan. This is advantageous, because indirect immobilization eliminates any interference with endoglycosidase activity that can be caused by direct immobilization of GAG chains.

Once the labeled proteoglycan is immobilized, the activity of an endoglycosidase corresponding to the GAG chains on the proteoglycan can be assayed. This can be done without a therapeutic agent to test the baseline activity of the endoglycosidase or with a therapeutic agent, such as an inhibitor or activator, to test the efficacy of the therapeutic agent. Once the therapeutic agent is added to the immobilized labeled proteoglycan in the multi-well plate (105), the GAG-specific endoglycosidase is also added to the multi-well plate (106). The sample in the multi-well plate is then incubated for enough time to allow the endoglycosidase to digest all of the GAG chains, if any, on the immobilized proteoglycan. Depending on the amount of endoglycosidase added to the proteoglycan, in some embodiments, the sample is incubated for thirty minutes. In other embodiments, the sample can be incubated for two hours or overnight.

After the endoglycosidase digestion is complete, the multi-well plate is rinsed in order to remove any digested ends of the labeled proteoglycan and to remove the endoglycosidase (107). Once the waste is removed, the immobilized proteoglycan can be detected to assay the activity of the endoglycosidase (108). In one embodiment, the proteoglycan is detected using ELISA with a reporter molecule such as streptavidin-conjugated horse radish peroxidase (streptavidin-HRP). ELISA detects the reducing-end labels of the GAG chains on the labeled proteoglycan. The strength of the signal detected corresponds to the activity of the endoglycosidase. The stronger the signal, the less GAG chains digested by the endoglycosidase. If, for example, a therapeutic agent has no inhibitive effect, all of the labeled ends of the GAG chains will be digested by the endoglycosidase and negligible signal will be detected from the proteoglycan.

Method 100 is thus advantageous, because it is highly sensitive and reproducible, and therefore suitable for screening potential GAG-specific endoglycosidase inhibitors and activators. Furthermore, unlike existing methods, method 100 provides a way to quantify endoglycosidase activity (described in greater detail in the examples below). Method 100 can also be performed using only nano-gram (ng) levels of a substrate proteoglycan and recombinant endoglycosidase. As a result, method 100 also allows for high throughput testing of endoglycosidase activity.

Figure 2:
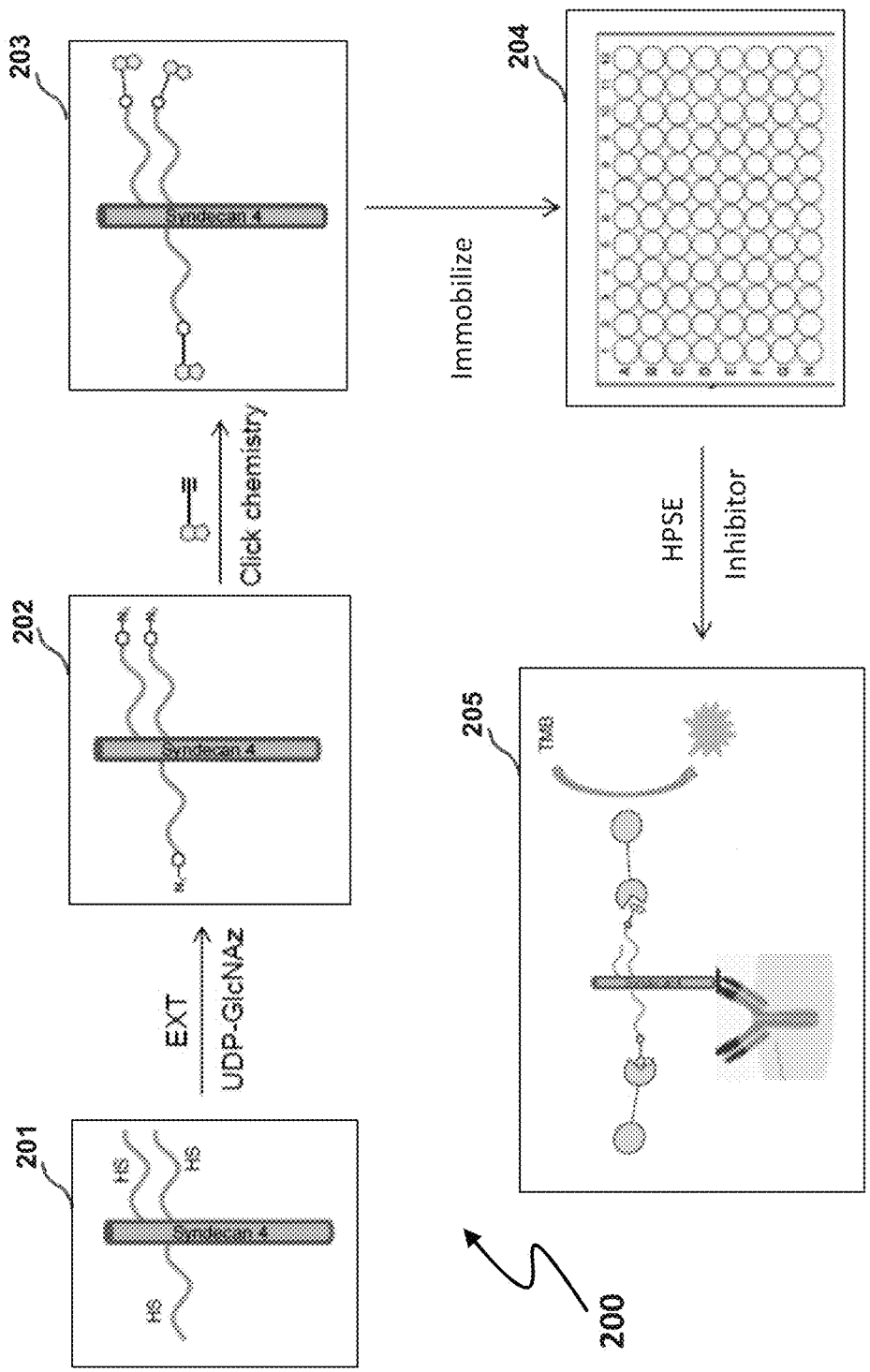
FIG. 2 is a flow diagram of a method for assaying heparanase activity according to various embodiments.

FIG. 2 is a flow diagram of method 200 for assaying heparanase (HPSE) activity. Method 200 is substantially similar to method 100 of FIG. 1, except method 200 is specific to assaying HPSE activity. Due to its role in cancer pathology, HPSE is an important endoglycosidase target for drug discovery. HPSE is a hydrolase and the only known enzyme that cleaves heparan sulfate (HS) in the extracellular matrix and cell membrane. HS is a linear polysaccharide found in the extracellular matrix and on the cell membrane and plays a role in a number of cellular events, including cell growth, migration, and differentiation. HS binds various growth factors, cytokines, and other extracellular matrix proteins. HPSE digestion of HS facilitates cell invasion and metastasis of cancer. Furthermore, the degradation of HS by HPSE releases HS-bound angiogenic growth factors, which promotes an angiogenic response. Method 200 is advantageous, because it can be used to screen potential HPSE inhibitors for use in preventing metastasis of cancer.

In method 200, a recombinant human Syndecan-4 with HS chains (201) is treated with EXT1/2 (a recombinant heterodimer glycosyltransferase) to incorporate GlcNAz into the non-reducing ends of the HS chains (202). A label is subsequently attached to the GlcNAz with a click chemistry reaction to form a labeled Syndecan-4 (203). In one embodiment, the label is a biotin-alkyne adduct. The labeled Syndecan-4 is then immobilized on a 96-well plate using an anti-human Syndecan-4 capture antibody (204). Once the labeled proteoglycan is immobilized, HPSE activity can be assayed. This can be done without a therapeutic agent to test the baseline activity of the HPSE or with a therapeutic agent, such as an inhibitor, to test the efficacy of the therapeutic agent.

Once the therapeutic agent is added to the Syndecan-4 in the multi-well plate, the HPSE is also added to the multi-well plate. The sample in the multi-well plate is then incubated for enough time to allow the HPSE to digest all of the HS chains, if any, on the immobilized Syndecan-4. Depending on the amount of HPSE added to the proteoglycan, in some embodiments, the sample is incubated for thirty minutes. In other embodiments, the sample can be incubated for two hours or overnight. After the HPSE digestion is complete, the multi-well plate is rinsed in order to remove any digested ends of the HS and to remove the HPSE. Once the waste is removed, the immobilized Syndecan-4 can be detected to assay the activity of the HPSE (205). In one embodiment, the HPSE is detected using ELISA with a streptavidin-conjugated horse radish peroxidase reporter molecule. ELISA detects the non-reducing end labels of the HS chains on the labeled proteoglycan. The strength of the signal detected corresponds to the activity of the HPSE. The stronger the signal, the less HS chains digested by the HPSE, which indicates less activity of HPSE.

EXAMPLES

Materials

Recombinant human EXT1/2 (an EXT1 and EXT2 heterodimer), Syndecan-4 (rhSynd4), UDP-GlcNAz (advertised as UDP-azido-GlcNAc), a Syndecan-4 DuoSet kit, suramin, biotin adduct D (advertised as biotinylated alkyne), recombinant HPSE, and a 96-well clear plate were obtained from Bio-Techne®. Biotin DIBO alkyne was obtained from Thermo Fisher Scientific®. Chrondroitin sulfate, heparin, bovine serum albumin, ascorbic acid, copper (II) chloride ($CuCl_2$), and dimethyl sulfoxide were obtained from Sigma-Aldrich®.

Example 1: HS Non-Reducing End Labeling of rhSynd4 for Sodium Dodecyl Sulfate Polyacrylamide Gel Electrophoresis (SDS-PAGE) and Silver Staining To label the non-reducing ends of HS chains on rhSynd4 with a clickable carbohydrate for SDS-PAGE and silver staining, 5 micrograms (μg) of rhSyn4 were mixed with 1 nanomol (nmol) of UDP-GlcNAz and 1 μg of EXT1/2 in a buffer of 25 microliters (μl) of 25 millimolar (mM) Tris, 150 mM NaCl, and 10 mM $MnCl_2$ at pH 7.5. The mixture was incubated at 37 degrees Celsius (° C.) for one hour to allow the EXT1/2 to attach the GlcNAz to the non-reducing ends of the HS chains on the rhSynd4. Subsequently, 5 nmol $CuCl_2$ and 100 nmol ascorbic acid (click chemistry reagents), along with 2 nmol biotin adduct D were added to the reaction, resulting in a final volume of 40 μl. A click chemistry reaction was performed at room temperature for 30 minutes to attach the biotin adduct D to the GlcNAz.

Figure 3:
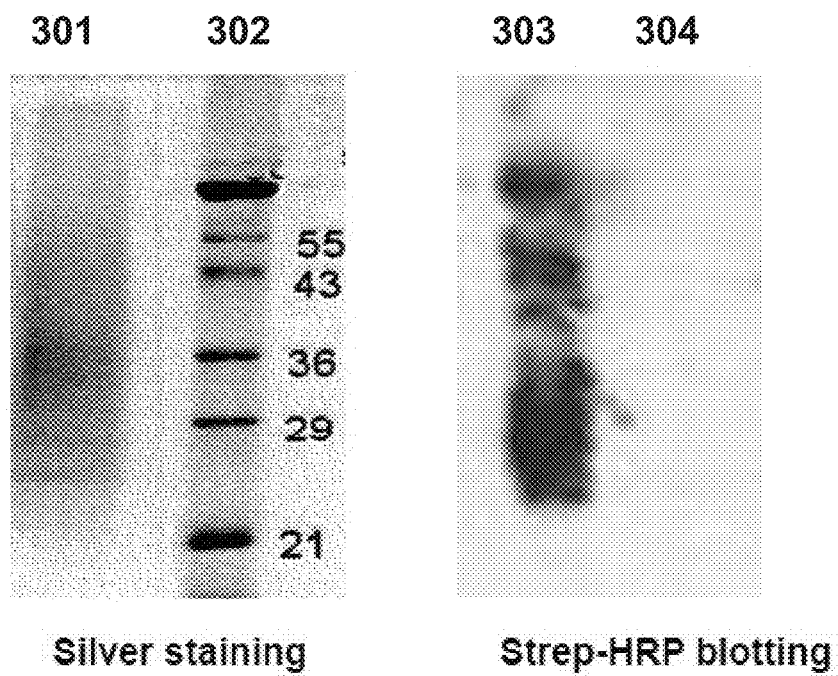
FIG. 3 shows images of the results of labeling recombinant human Syndecan-4 with GlcNAz.

Half of the final product was subjected to SDS-PAGE, blotted into a nitrocellulose membrane, and visualized with streptavidin-HRP. For comparison, unlabeled rhSynd4 was run separately in SDS-PAGE and visualized by a silver staining method. The results are shown in FIG. 3. Lane 301 shows silver staining of unlabeled rhSynd4, and lane 302 shows molecular markers for comparison. Lane 303 shows streptavidin-HRP blotting of the biotin-labeled rhSynd4, and lane 304 shows unlabeled rhSynd4 for comparison. FIG. 3 confirms the unexpected results that the non-reducing end of HS on rhSynd4 can be labeled with GlcNAz using EXTs and click chemistry.

Example 2: HS Non-Reducing End Labeling of rhSynd4 for ELISA

To label the non-reducing ends of HS chains on rhSynd4 with a clickable carbohydrate for ELISA, 2 μg of rhSyn4 were mixed with 5 nmol of UDP-GlcNAz and 5 µg of EXT1/2 in a buffer of 400 µl of 25 mM Tris, 150 mM NaCl, and 10 mM $Mn^{2+}$ at pH 7.5. The mixture was incubated at 37° C. for one hour to allow the EXT1/2 to attach the GlcNAz to the non-reducing ends of the HS chains on the rhSynd4. Subsequently, 10 µl of 1 mM biotin DIBP alkyne in dimethyl sulfoxide (click chemistry reagent) were added to the reaction, resulting in a final volume of 410 µl. Biotin DIBP alkyne is a copper-free click chemistry reagent used to prevent any toxicity of copper to an HPSE digestion reaction. A click chemistry reaction was performed overnight in the dark at room temperature to attach the biotin adduct D to the GlcNAz. The final product was diluted 8 fold in a buffer of 50 mM NaAc at pH 4.0.

Example 3: Detecting HS Non-Reducing End Labeled rhSynd4 with ELISA

In order to establish a high throughput compatible method for HS detection, an ELISA assay was used to attempt to detect labeled rhSynd4. The non-reducing ends of HS chains on rhSynd4 were labeled according to Example 2 above. Increasing amounts of the labeled rhSynd4 (0-50 ng) were subsequently immobilized on a 96-well plate coated with 80 ng/well of goat anti-human Syndecan-4 capture antibody. The Syndecan-4 DuoSet kit was used to perform an ELISA assay (described in detail in Example 4 below). The absorbance (OD 450) of each well was determined using a microplate reader set to 450 nanometers (nm).

Figure 4:
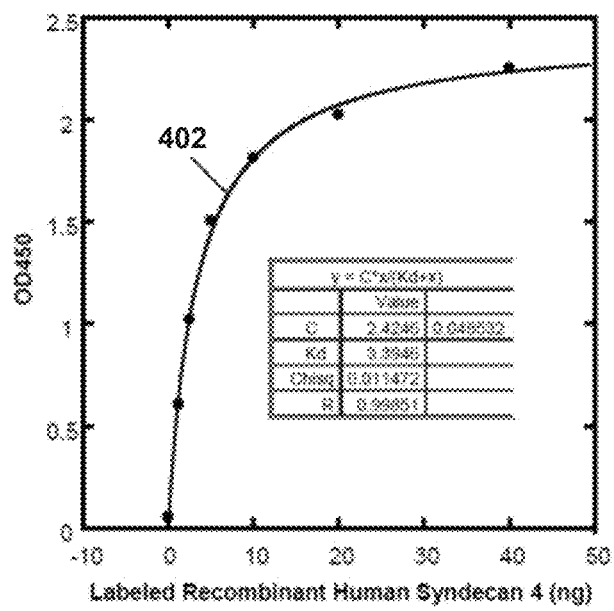
FIG. 4 is a graph of the absorbance at 450 nanometers of increasing amounts of labeled recombinant Syndecan-4.

FIG. 4 is a graph of the OD 450 of increasing amounts of labeled rhSynd4. The data was fit to the equation $y=Cx/(K_d+x)$ to obtain curve 402, where $K_d$ is the ligand-receptor binding affinity (dissociation constant for rhSynd4 bound to the capture antibody). Based on curve 402, the $K_d$ was found to be 3.4 ng, confirming that labeled rhSynd4 can be detected using ELISA.

Example 4: Validation of High Throughput HPSE Activity Assay

HPSE was diluted into a series of concentrations in 50 mM NaAc at pH 4.0. For each concentration, ten µl of diluted HPSE was mixed with 10 µl of labeled rhSynd4 from Example 2. The mixture was incubated at 37° C. for twenty minutes to allow the HPSE to digest the labeled HS chains on the rhSynd4. The HPSE treated mixture was subsequently heated at 95° C. for two minutes to stop the digestion reaction. The Syndecan-4 DuoSet kit was used to perform an ELISA assay on the HPSE treated mixture to establish a high throughput method for detection of HS, which correlates to HPSE digestion of HS.

In order to prepare the sample for the assay, the goat anti-human Syndecan-4 capture antibody was diluted to a working concentration in PBS without carrier protein. A 96-well microplate was immediately coated with 100 µL per well of the diluted capture antibody. The plate was sealed and incubated overnight at room temperature. Each well was subsequently aspirated and washed with wash buffer, repeating the process two times for a total of three washes. The wash buffer is 25 mM Tris (pH 7.6), 137 mM NaCl, and 0.01% Tween (TBST). Each well was washed by filling each well with 400 µL of wash buffer using a squirt bottle, manifold dispenser, or autowasher. After the last wash, any remaining wash buffer was removed by aspirating or by inverting the plate and blotting it against clean paper towels. The microplate was then blocked by adding 300 µL of reagent diluent to each well and incubating the microplate for a minimum of 1 hour. The microplate was then aspirated/washed as described above for a total of three washes, and the microplate was thus ready for sample addition.

To perform the ELISA assay, 100 µL of the HPSE treated mixture diluted with 1% BSA in PBS buffer were added per well. The HPSE treated mixture was diluted such that the concentration of rhSynd4 was 25 ng/ml. The microplate was covered with an adhesive strip and incubated 2 hours at room temperature. The microplate was then aspirated/washed as described above for a total of three washes and 100 µL of working dilution of Streptavidin-HRP was added to each well. The microplate was covered and incubated for 20 minutes at room temperature. The microplate was then aspirated/washed as described above for a total of three washes, and 100 µL of HRP substrate solution was added to each well. The microplate was covered and incubated for 20 minutes at room temperature. Fifty µL of stop solution was subsequently to each well, and the plate was gently tapped to ensure thorough mixing.

Figure 5:
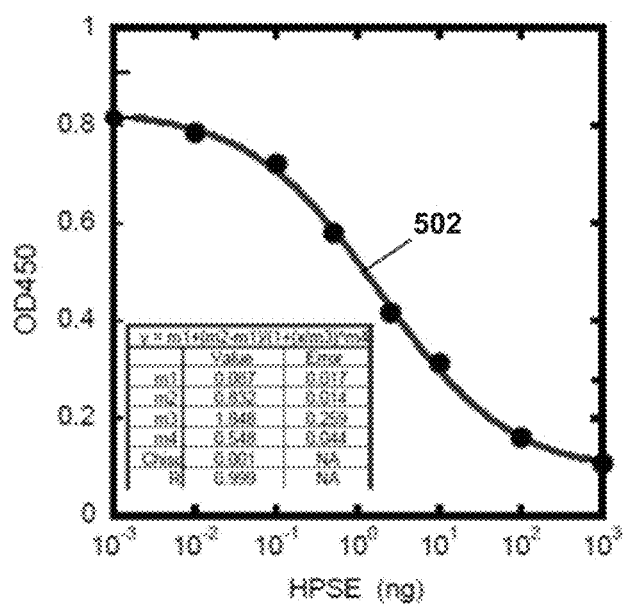
FIG. 5 is a graph of the absorbance at 450 nanometers of labeled recombinant Syndecan-4 digested with increasing amounts of heparanase.

The absorbance (OD 450) of each well was determined using a microplate reader set to 450 nm. FIG. 5 is a graph of the OD 450 of labeled rhSynd4 digested with increasing amounts of HPSE. The data was fit to the equation $y=m_1+(m_2-m_1)/(1+(x/m_3)\char`\^m_4)$ to obtain a typical digestion curve 502, where $m_3$ is the half-maximal effective value of HPSE digestion of HS (EC50). Based on curve 502, the EC50 was found to be 1.85 ng, which indicates that the HPSE activity assay of this disclosure is much more sensitive than, for example, an HPSE radioisotope assay, which is known to have an EC50 of 10 ng. This also confirms that the HPSE activity assay of this disclosure is high throughput compatible.

In order to further validate the HPSE assay of this disclosure, a Z-factor analysis was performed. Z-factor is a coefficient reflective of both the assay signal dynamic range and the data variation associated with signal measurements, and therefore is suitable for assay quality assessment. Z-factor is a dimensionless statistical characteristic for an assay that provides a useful tool for comparison and evaluation of the quality of assays. Z-factor is utilized in assay optimization and validation. In high throughput screening, Z-factor is referred to as Z'. Z' is determined using the equation $Z'=1-(3\sigma_{c+}+3\sigma_{c-})/|\mu_{c+}-\mu_{c-}|$, where $\sigma_{c+}$ and $\sigma_{c-}$ are standard deviations of positive and negative controls, and $\mu_{c+}$ and $\mu_{c-}$ are the means of the positive and negative controls.

To determine the Z' factor for the HPSE assay, 2.5 ng of labeled rhSynd4 from Example 2 was digested with either 10 ng or 100 ng of HPSE in 100 µl of acetate buffer at pH 4.0 for two hours at 37° C. This resulted in two positive controls—labeled rhSynd4 digested with 10 ng of HPSE and labeled rhSynd4 digested with 100 ng HPSE. The labeled rhSynd4 was then immobilized to a goat anti-human Syndecan-4 coated 96-well plate and assayed with ELISA as described above in Example 3. A sample without HPSE digestion (negative control) was also assayed with ELISA for comparison. 32 samples of each of the positive controls and the negative control were assayed with ELISA.

Figure 6:
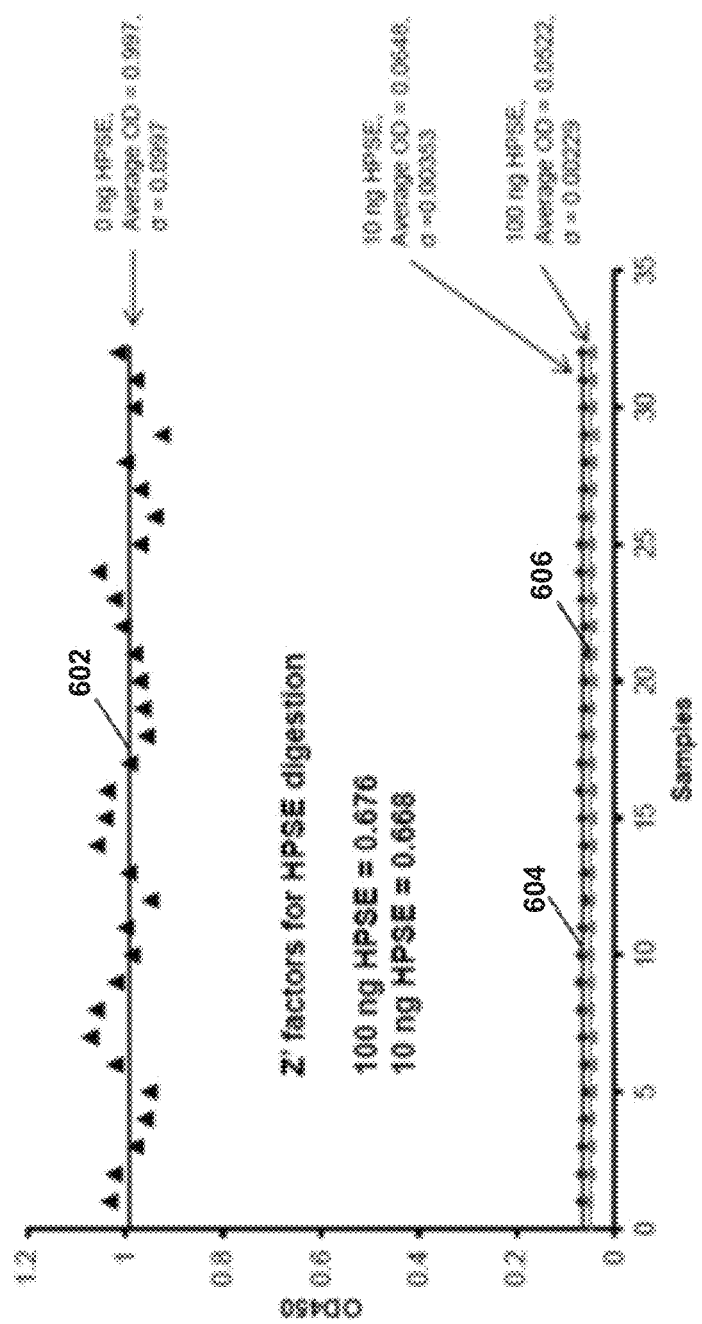
FIG. 6 is a graph of the absorbance at 450 nanometers of undigested labeled Syndecan-4, Syndecan-4 digested with 10 nanograms of heparanase, and Syndecan-4 digested with 100 nanograms of heparanase.

FIG. 6 is a graph of the OD 450 of the samples of undigested labeled rhSynd4 (602), labeled rhSynd4 digested with 10 ng of HPSE (604), and labeled rhSynd4 digested with 100 ng of HPSE (606). Using the equation above, Z' was calculated for HPSE digestion. As shown in FIG. 6, the $\sigma_{c-}$ for the undigested labeled rhSynd 4 is 0.0997 and the is 0.997. The $\sigma_{c+}$ for the labeled rhSynd4 digested with 10 ng of HPSE is 0.00353 and the is 0.0648, resulting in a Z' of 0.668. The $\sigma_{c+}$ for the labeled rhSynd4 digested with 100 ng of HPSE is 0.00229 and the is 0.0522, resulting in a Z' of 0.676. These Z' factors validate the method disclosed for assaying HPSE activity and confirmed its consistency and suitability for high throughput screening of therapeutic agents.

Example 5: HPSE Inhibitor Study

HS proteoglycans are major constituents of the endothelial cell plasma membrane in the interior surface of blood vessels. Investigation of transformed or tumorigenic cells has shown that increased HPSE activity can correspond to increased metastatic potential. As a result, HPSE inhibitors are of particular interest in cancer therapies. The HPSE Activity assay of Example 4 was performed to determine the efficacy of three compounds: suramin (a known HSPE inhibitor), heparin (structurally similar to HS), and chondroitin sulfate (structurally similar to HS).

In order to determine the efficacy of each inhibitor, increasing amounts of the inhibitor was mixed with 10 ng HPSE in 10 µl of 50 mM NaAc at pH 4.0. The inhibitor/HPSE mixture was then mixed with 10 µl of labeled rhSynd4 from Example 2 and incubated at 37° C. for two hours to allow the HPSE to digest the labeled HS chains on the rhSynd4. The inhibitor/HPSE treated mixture was subsequently heated at 95° C. for two minutes to stop the digestion reaction. The Syndecan-4 DuoSet kit was used to perform an ELISA assay on the inhibitor/HPSE treated mixture as described above in Example 3.

Figure 7:
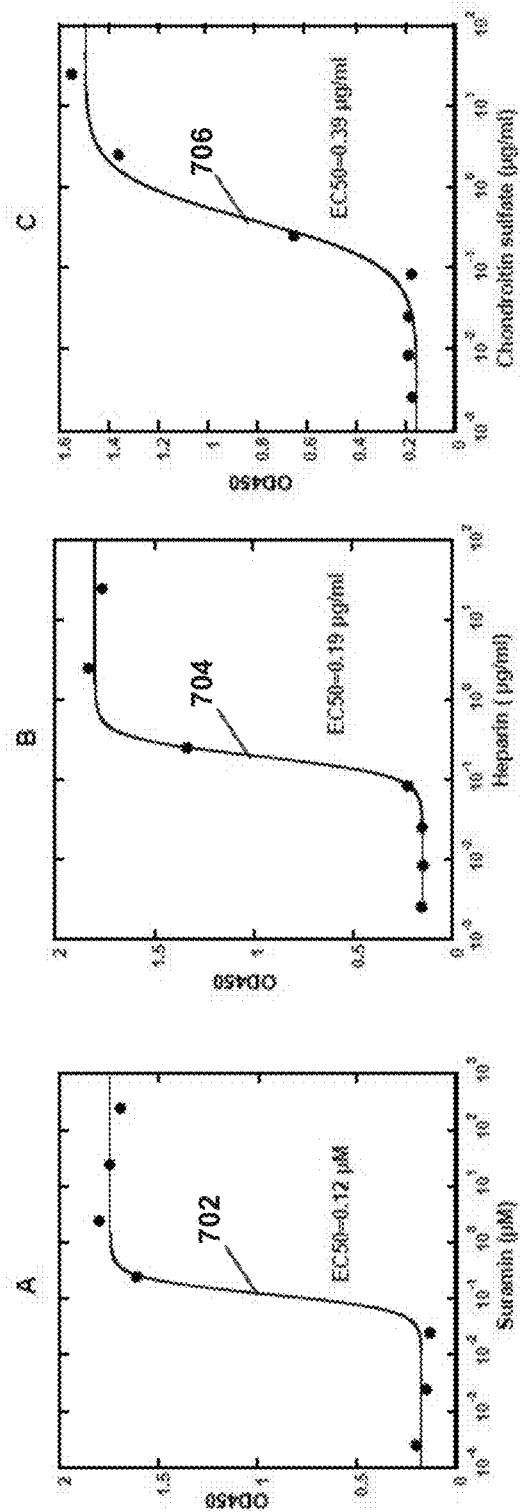
FIGS. 7A-7C are graphs of the absorbance at 450 nanometers of labeled recombinant Syndecan-4 digested with heparanase in the presence of different amounts of suramin (FIG. 7A), heparin (FIG. 7B), and chondroitin sulfate (FIG. 7C).

The absorbance (OD 450) for each of the three compounds was determined using a microplate reader set to 450 nm. FIGS. 7A-7C are graphs of the OD 450 of labeled rhSynd4 digested with HPSE in the presence of different amounts of suramin (FIG. 7A), heparin (FIG. 7B), and chondroitin sulfate (FIG. 7C). For each compound, the data was fit to the equation $y=m_1+(m_2-m_1)/(1+(x/m_3)^{\wedge}m_4)$ to obtain curves 702, 704, and 706 where $m_3$ is the EC50 for the compound. EC50 is a measure of the effectiveness of a drug or inhibitor. The EC50 of a substance gives the concentration of that substance required to achieve 50 percent of its maximum effect. The EC50 for suramin was determined to be 0.12 µM. The EC50 for heparin was determined to be 0.12 µg/ml, and the EC50 for chondroitin sulfate was determined to be 0.39 µg/ml.

Example 6: Detecting Keratan Sulfate (KS)
Non-Reducing End Labeled Recombinant Lumican
and KS Specific Endogalactosidase (KSEG)
Activity with ELISA This study confirmed that the endoglycosidase activity assay of this disclosure is applicable to other endoglycosidases in addition to HPSE. An ELISA assay was first used to detect labeled recombinant lumican. The non-reducing ends of KS chains on recombinant human lumican were labeled through in vitro incorporation of GlcNAz by B3GNT2 (a KS specific GlcNAc transferase) according to the procedure described in Example 2 above. Increasing amounts of the labeled lumican (0-100 ng) were subsequently immobilized on a 96-well plate coated with 80 ng/well of goat anti-human lumican capture antibody.

Figures 8, 9:
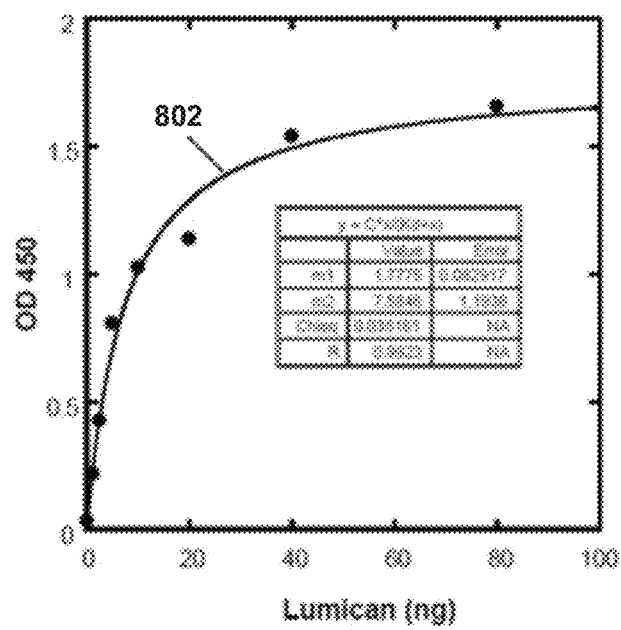
FIG. 8 is a graph of the absorbance at 450 nanometers of increasing amounts of labeled recombinant lumican at 450 nanometers.
FIG. 9 is a graph of the absorbance at 450 nanometers of labeled recombinant lumican digested with increasing amounts of keratan sulfate specific endogalactosidase.

A DuoSet ELISA kit of Human Lumican was used to perform an ELISA assay similarly to the procedure described in Example 4 above. The absorbance (OD 450) of each well was determined using a microplate reader set to 450 nm. FIG. 8 is a graph of the OD 450 of increasing amounts of labeled lumican. The data was fit to the equation $y=Cx/(K_d+x)$ to obtain curve 802, where $K_d$ is the ligand-receptor binding affinity (dissociation constant for lumican bound to the capture antibody). Based on curve 802, the $K_d$ was found to be 7.58 ng, confirming that labeled lumican can be detected using ELISA.

An ELISA was subsequently used to detect the digestion of KS by KSEG. Twenty ng of the labeled recombinant lumican described above were digested with increasing amount of KSEG cloned from *F. keratolyticus* and subsequently immobilized on a 96-well plate coated with 80 ng/well of goat anti-human lumican capture antibody. A DuoSet ELISA kit of Human Lumican was used to perform an ELISA assay similarly to the procedure described in Example 4 above. The absorbance (OD 450) of each well was determined using a microplate reader set to 450 nm.

FIG. 9 is a graph of the OD 450 of labeled lumican digested with increasing amounts of KSEG. The data was fit to the equation $y=m_1+(m_2-m_1)/(1+(x/m_3)^{\wedge}m_4)$ to obtain a typical digestion curve 902, where $m_3$ is the half-maximal effective value of KSEG digestion of KS (EC50). Based on curve 902, the EC50 was found to be 49 ng, which confirms that the endoglycosidase activity assay of this disclosure is applicable to other endoglycosidases in addition to HPSE.

The invention claimed is:

1. A method for assaying endoglycosidase activity, the method comprising:
   providing a proteoglycan having a glycosaminoglycan chain with a non-reducing end;
   treating the proteoglycan with a glycosyltransferase to incorporate a carbohydrate into the non-reducing end of the glycosaminoglycan chain, wherein the carbohydrate includes a click chemistry moiety;
   adding a label to the proteoglycan, wherein the label includes a click chemistry moiety that reacts to the click chemistry moiety of the carbohydrate such that the label attaches to the carbohydrate to form a labeled proteoglycan;
   immobilizing the labeled proteoglycan on a multi-well plate, wherein the multi-well plate includes a specific anti-proteoglycan antibody for binding the labeled proteoglycan;
   treating the labeled proteoglycan with an endoglycosidase specific to the glycosaminoglycan chain; and
   detecting the labeled proteoglycan immobilized on the multi-well plate.

2. The method of claim 1, wherein the proteoglycan is a recombinant proteoglycan, the glycosyltransferase is a recombinant glycosyltransferase, and the endoglycosidase is a recombinant endoglycosidase.

3. The method of claim 1, wherein the proteoglycan is selected from the group consisting of Syndecan-1, Syndecan-2, Syndecan-3, Syndecan-4, Glypican-1, Glypican-2, Glypican-3, Glypican-4, Glypican-5, Glypican-6, lumican, mimican, aggrecan, Testican 1, Testican 2, and Testican 3.

4. The method of claim 1, wherein the glycosaminoglycan chain is selected from the group consisting of heparan sulfate, heparin, chondroitin sulfate, dermatan sulfate, keratan sulfate, and hyaluronan.

5. The method of claim 1, wherein the glycosyltransferase is a selected from the group consisting of GlcNAc transferase, GalNAc transferase, galactosyltransferase, glucuronosyltransferase, and combinations thereof.

6. The method of claim 1, wherein the glycosyltransferase is an EXT1/2 heterodimer and the carbohydrate is GlcNAz.

7. The method of claim 1, wherein the carbohydrate includes a click chemistry moiety selected from one of an azido group or an alkyne group and the label includes a click chemistry moiety selected from the other of the azido group or the alkyne group.

8. The method of claim 1, wherein the label includes a colorimetric molecule, a biotin molecule, a fluorogenic molecule, or a luminescent molecule.

9. The method of claim 1, wherein the endoglycosidase is selected from the group consisting of heparanase, sperm adhesion molecule 1, hyaluronidase 1, hyaluronidase 2, hyaluronidase 3, hyaluronidase 4, and keratan sulfate specific endo-beta-galactosidase.

10. The method of claim 1, further comprising adding an inhibitor or a drug to the labeled proteoglycan.

11. The method of claim 1, wherein the labeled proteoglycan is detected with an enzyme-linked immunosorbent assay using a reporter molecule, wherein the reporter molecule is a streptavidin-conjugated horse radish peroxidase.

12. The method of claim 1,
wherein the proteoglycan having a glycosaminoglycan chain with a non-reducing end is a recombinant human Syndecan-4 having a heparan sulfate with a non-reducing end;
wherein the glycosyltransferase is EXT1/2 heterodimer and the carbohydrate is GlcNAz;
wherein the label includes an alkyne group click chemistry moiety that reacts to the click chemistry moiety of the GlcNAz such that the label attaches to the GlcNAz to form a labeled Syndecan-4;
wherein the specific anti-proteoglycan antibody on the multi-well plate is a specific anti-Syndecan-4 antibody for binding the labeled Syndecan-4; and
wherein the endoglycosidase is heparanase.

13. A kit for assaying endoglycosidase activity, the kit comprising:
a proteoglycan having a glycosaminoglycan chain with a non-reducing end;
a carbohydrate with a click chemistry moiety;
a glycosyltransferase configured to incorporate the carbohydrate into the non-reducing end of the glycosaminoglycan chain;
a label including a click chemistry moiety that reacts to the click chemistry moiety of the carbohydrate such that the label attaches to the carbohydrate;
an endoglycosidase specific to the glycosaminoglycan chain;
a specific anti-proteoglycan antibody for binding the labeled proteoglycan;
a multi-well plate, wherein multi-well plate includes the specific anti-proteoglycan antibody for binding the labeled proteoglycan;
click chemistry reagents; and
a reporter molecule.

14. The kit of claim 13, wherein:
the proteoglycan is a Syndecan-4 having a heparan sulfate;
the glycosyltransferase is an EXT1/2 heterodimer;
the carbohydrate is GlcNAz having an azido group click chemistry moiety;
the label includes an alkyne group click chemistry moiety that reacts to the click chemistry moiety of the GlcNAz such that the label attaches to the GlcNAz;
the endoglycosidase is a heparanase;
the anti-proteoglycan antibody is an anti-Syndecan-4 antibody; and
the reporter molecule is a streptavidin-conjugated horse radish peroxidase.

15. The kit of claim 13, wherein the glycosaminoglycan chain is selected from the group consisting of heparan sulfate, heparin, chondroitin sulfate, dermatan sulfate, keratan sulfate, and hyaluronan.

16. The kit of claim 13, wherein the endoglycosidase is selected from the group consisting of heparanase, sperm adhesion molecule 1, hyaluronidase 1, hyaluronidase 2, hyaluronidase 3, hyaluronidase 4, and keratan sulfate specific endo-beta-galactosidase.

17. The kit of claim 13, wherein the glycosyltransferase is selected from the group consisting of GlcNAc transferase, GalNAc transferase, galactosyltransferase, glucuronosyltransferase, and combinations thereof.

18. The kit of claim 13, wherein the endoglycosidase is a recombinant endoglycosidase and the glycosyltransferase is a recombinant glycosyltransferase.

19. The kit of claim 13, wherein the glycosyltransferase is an EXT1/2 heterodimer.

* * * * *